US00PP30005P2

(12) United States Plant Patent
Ammerlaan

(10) Patent No.: US PP30,005 P2
(45) Date of Patent: Dec. 18, 2018

(54) ***ECHEVERIA* PLANT NAMED 'OVPEARLS01'**

(50) Latin Name: ***Echeveria* hybrid**
Varietal Denomination: OVPEARLS01

(71) Applicant: Johannes Hendrikus Adrianus Ammerlaan, Bleiswijk (NL)

(72) Inventor: Johannes Hendrikus Adrianus Ammerlaan, Bleiswijk (NL)

(73) Assignee: Ovata B.V., Bleiswijk (NL)

( * ) Notice: Subject to any disclaimer, the term of this patent is extended or adjusted under 35 U.S.C. 154(b) by 0 days.

(21) Appl. No.: 15/731,953

(22) Filed: Aug. 31, 2017

(30) Foreign Application Priority Data

Jul. 18, 2017 (QZ) ..... PBR 2017/1809

(51) Int. Cl.
*A01H 5/12* (2018.01)

(52) U.S. Cl.
USPC ..... Plt./373
CPC ..... *A01H 5/12* (2013.01)

(58) Field of Classification Search
USPC ..... Plt./373
See application file for complete search history.

*Primary Examiner* — Anne Marie Grunberg
(74) *Attorney, Agent, or Firm* — Samuel R. McCoy, Jr.

(57) ABSTRACT

A new and distinct cultivar of *Echeveria* plant named 'OVPEARLS01' which is characterized by a flattened globular plant form with strongly concaved to cup-shaped foliage which is held upright. The foliage is greyed-purple with narrow pink margins and ages to greyed-brown with narrow pink margins, and is moderately pruinose which creates a distinct bluish hue. The new variety has shown to be uniform and stable in the resulting generations from asexual propagation.

4 Drawing Sheets

Latin name of the genus and species: The Latin name of the genus and species of the novel variety disclosed herein is *Echeveria* hybrid.

Variety denomination: The inventive variety of *Echeveria* disclosed herein has been given the variety denomination 'OVPEARLS01'.

CROSS REFERENCE TO RELATED APPLICATIONS

This application claims priority to the Community Plant Variety Rights application number 2017/1809, filed on Jul. 18, 2017, which is herein incorporated by reference.

BACKGROUND OF THE INVENTION

Parentage: 'OVPEARLS01' is a spontaneous whole-plant mutation of *Echeveria* 'Perle Von Nürnberg' (not patented) which was discovered by the inventor in March of 2015 at a commercial greenhouse in Bleiswijk, the Netherlands. The mutation was noted for its blue-hued, strongly concaved foliage.

Asexual Reproduction: Asexual reproduction of the new cultivar 'OVPEARLS01', by way of rooting leaf cuttings, was first initiated in March of 2015 at the inventor's commercial greenhouse in Bleiswijk, the Netherlands. Through five subsequent generations, the unique features of this cultivar have proven to be stable and true to type.

SUMMARY OF THE INVENTION

The cultivar 'OVPEARLS01' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'OVPEARLS01'. These characteristics in combination distinguish 'OVPEARLS01' as a new and distinct *Echeveria* cultivar:

1. 'OVPEARLS01' exhibits a flattened globular plant form with foliage arranged in a basal rosette which eventually forms a short, unbranched stem with age; and
2. 'OVPEARLS01' exhibits broad spatulate foliage, held upright, which is strongly concaved to cup-shaped; and
3. 'OVPEARLS01' exhibits moderately pruinose foliage, which gives the foliage a bluish hue; and
4. 'OVPEARLS01' exhibits juvenile foliage with a greyed-purple general coloration, suffused with red towards the base, and narrow pink margins; and
5. 'OVPEARLS01' exhibits mature foliage with a brown to greyed-brown general coloration, suffused with red towards the base, and narrow pink margins.

BOTANICAL DESCRIPTION OF THE PLANT

Figure 1:
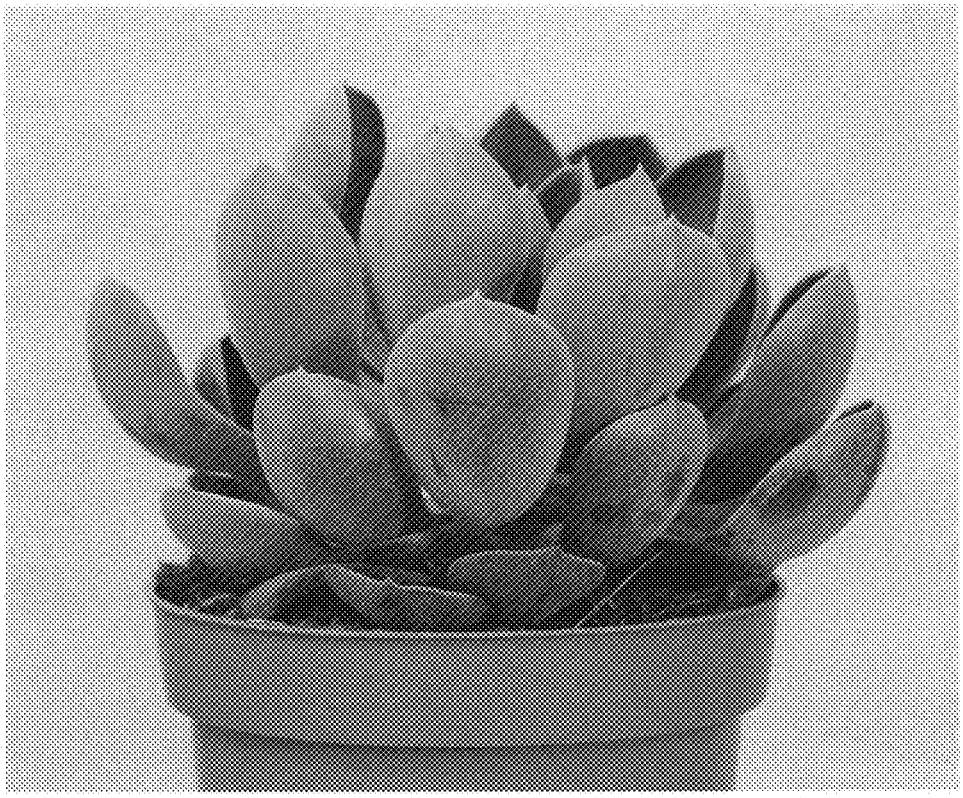
FIG. 1 illustrates, as nearly true as it is reasonably possible to make the same in color photographs of this type, an exemplary plant of 'OVPEARLS01' grown in a commercial greenhouse in Bleiswijk, the Netherlands. This plant is approximately 25 weeks old, shown planted in a 10.5 cm container.
Figure 2:
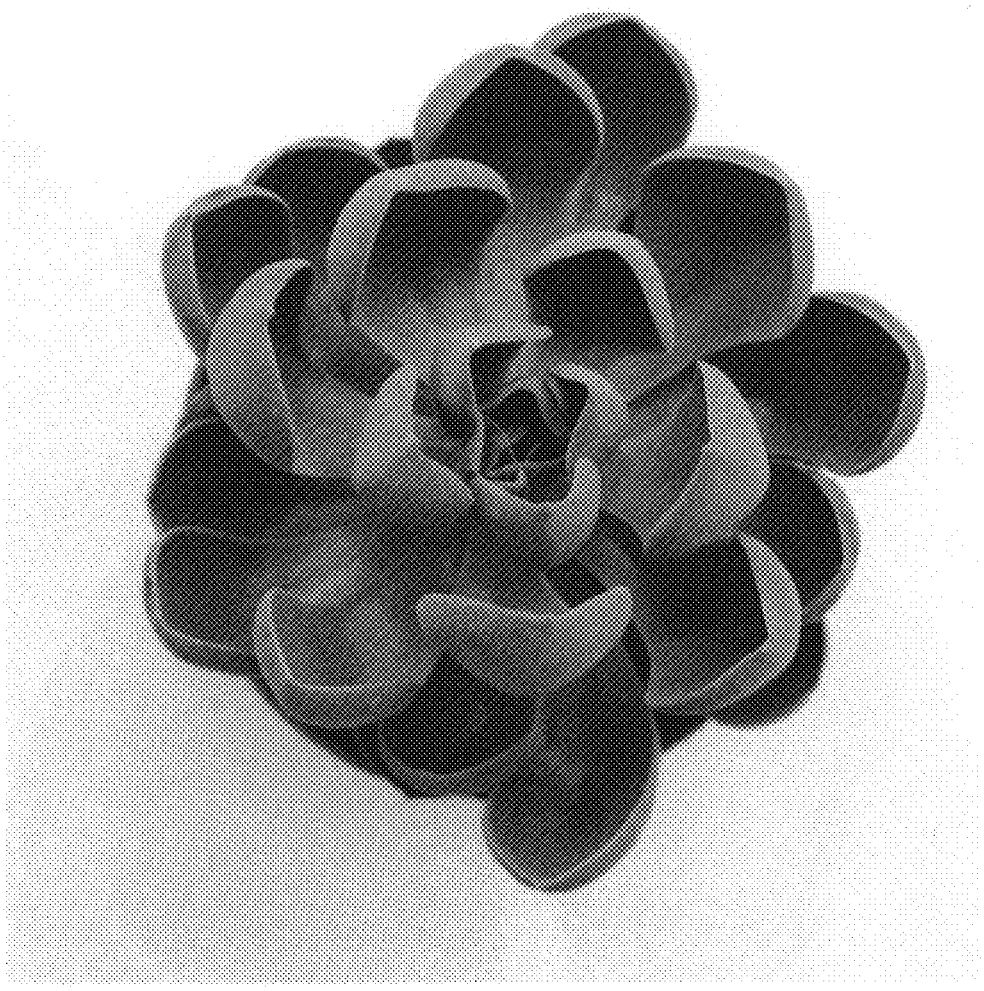
FIG. 2 illustrates, as nearly true as it is reasonably possible to make the same in color photographs of this type, the typical foliage arrangement of 'OVPEARLS01'.
Figure 3:
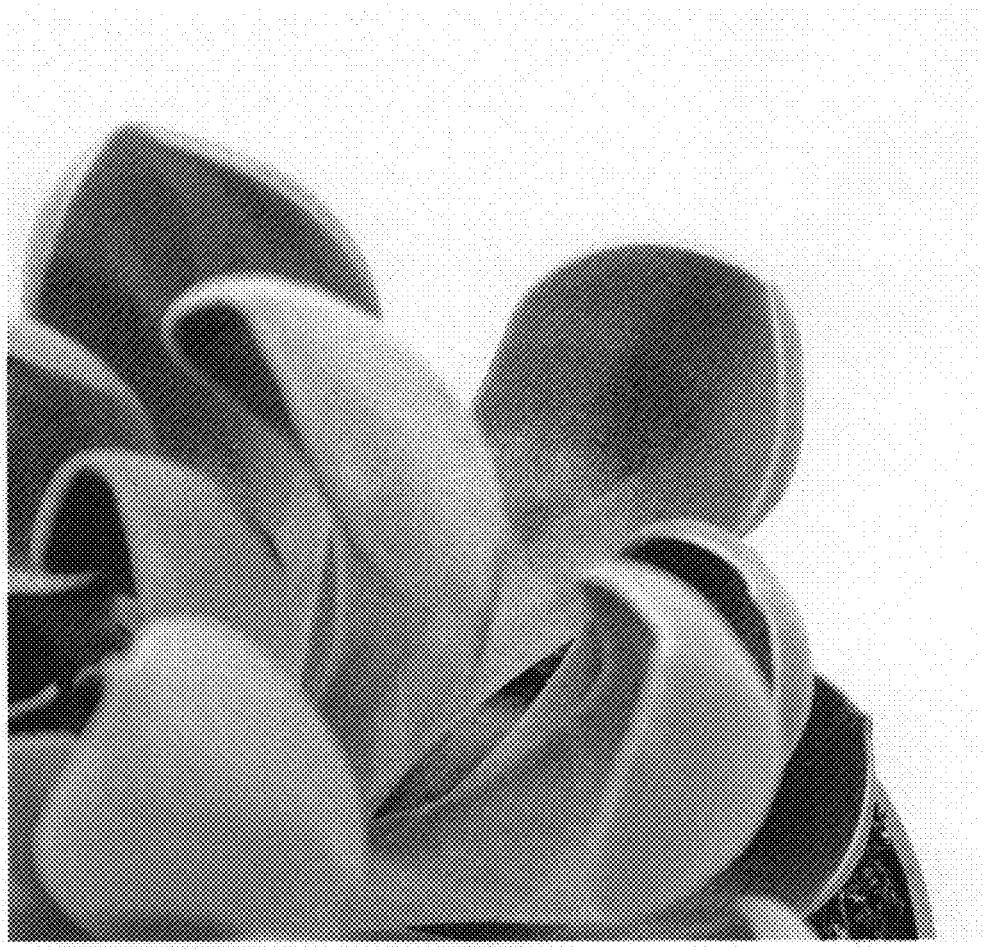
FIG. 3 illustrates, as nearly true as it is reasonably possible to make the same in color photographs of this type, the adaxial surface of the mature foliage 'OVPEARLS01'.
Figure 4:
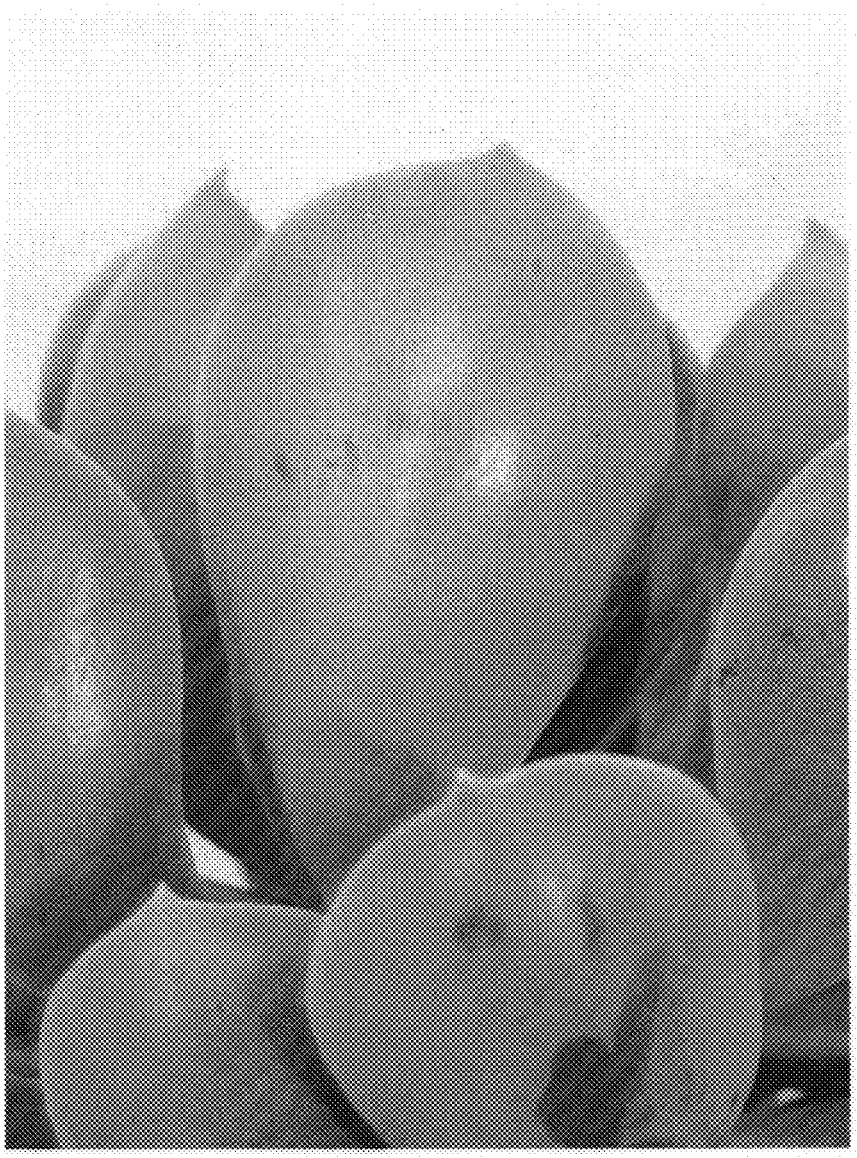
FIG. 4 illustrates, as nearly true as it is reasonably possible to make the same in color photographs of this type, the abaxial surface of the mature foliage 'OVPEARLS01'.

The following observations and measurements made in November of 2016 describe averages from a sample set of six specimens of 25 week old 'OVPEARLS01' plants grown in 10.5 cm nursery containers at commercial greenhouse in Bleiswijk, the Netherlands. Plants were produced using conventional greenhouse production protocols for *Echeveria* which consisted of minimal irrigation, by way of ebb and flow benches, and fertilizer applications. No chemical pest and disease control were utilized. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'OVPEARLS01' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'OVPEARLS01' and a comparison with the parent and closest known comparator is provided below.

Plant description:

*Growth habit*.—Succulent perennial with foliage growing in a non-branched basal rosette.

*Plant shape*.—Flattened globular.

*Height from soil level to top of foliar plane*.—10.0 cm.

*Plant spread*.—*Average of* 14.7 cm.

*Growth rate*.—Low.

*Plant vigor*.—Low.

*Propagation*.—Type — Leaf cuttings. Time to initiate rooting — Approximately 30 days at an approximate temperature of 20 degrees Celsius. Crop time — Approximately 25 weeks to produce a marketable plant in a 10.5 cm container.

*Disease and pest resistance or susceptibility*.—Neither resistance nor susceptibility to typical *Echeveria* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—Leaves in a basal rosettes, eventually forming a short, unbranched stem with age; no lateral branching.

*Quantity of main stems*.—1.

*Main stem dimensions*.—5.8 cm long and 1.3 cm in diameter.

*Internode length*.—0.2 cm.

*Cross section*.—Rounded.

*Aspect*.—Nearly vertical.

*Strength*.—Moderately strong.

*Texture and luster*.—Glabrous and matte, due to a waxy layer covering the stem.

*Color, when developing*.—Yellow-green, nearest to RHS 150D; stem covered with a waxy layer colored purple, nearest to RHS 76D.

*Color of mature stem*.—Red-purple, nearest to RHS 65C; stem covered with a waxy layer colored purple, nearest to RHS 76D.

*Color at internodes*.—Red-purple, nearest to RHS 65C; stem covered with a waxy layer colored purple, nearest to RHS 76D.

Foliage:

*Arrangement*.—Rosette.

*Division*.—Simple.

*Attachment*.—Sessile.

*Quantity*.—Approximately 33 leaves per rosette.

*Shape*.—Thick, succulent leaves which are spatulate.

*Dimensions*.—7.0 cm long, 3.1 cm wide, and 0.4 cm thick, on average.

*Aspect*.—Strongly concave to cup-shaped. Distal half of the leaf is curled upward at an average angle of 60 degrees to the proximal half.

*Attitude*.—Leaves are held upright.

*Apex*.—Short apiculate.

*Base*.—Narrow cuneate.

*Margin*.—Entire; not undulated or lobed.

*Pubescence, texture and luster of the adaxial surface*.—Glabrous, smooth, and slightly glossy; moderately pruinose, colored nearest to a mixture of greyed-purple to black, RHS N187B and 202B, but appearing as more of a bluish coloration (no correlating to an RHS color designation).

*Pubescence, texture and luster of the abaxial surface*.—Glabrous, smooth, and slightly glossy; moderately pruinose, colored nearest to greyed-purple, RHS N187B, but appearing as more of a bluish coloration (no correlating to an RHS color designation).

*Color*.—Juvenile foliage, adaxial surface — Greyed-purple, nearest to in between RHS N186C and 184A, and suffused with red towards the base, nearest to RHS 55B. Juvenile foliage, abaxial surface — Greyed-purple, in between RHS N186C and 187A, and suffused with red towards the base, in between RHS 53D. Mature foliage, adaxial surface — Brown, nearest to RHS N200A, and lightly suffused with yellow-green, nearest to RHS 148A; fading to greyed-red towards the base, nearest to in between RHS 181B and 181C; narrowly margined greyed-red, nearest to RHS 181A. Mature foliage, abaxial surface — Greyed-brown, RHS N199B; fading to greyed-red towards the base, nearest to in between RHS 181A and 181B; narrowly margined greyed-purple, nearest to RHS 183C.

*Venation*.—Pattern — No venation is visible. Color, adaxial surface — No venation is visible. Color, abaxial surface — No venation is visible.

*Petiole*.—No petiole; leaves are sessile.

Inflorescence: No flowering has been observed to date.

COMPARISONS WITH THE PARENT PLANT

Plants of the new cultivar 'OVPEARLS01' differ from the parent, *Echeveria* 'Perle Von Nürnberg' in the following characteristics described in Table 1 below.

TABLE 1

| Characteristic | 'OVPEARLS01' | 'Perle Von Nürnberg' |
|---|---|---|
| Leaf size. | Smaller than that of 'Perle Von Nürnberg'. | Larger than 'OVPEARLS01'. |
| Leaf aspect. | More concave. | Less concave. |
| General coloration of the mature foliage. | More greyed-purple; more pruinose. | Less greyed-purple; less pruinose. |
| Leaf margin coloration. | Red-purple. | Pink. |

COMPARISONS WITH THE CLOSEST KNOWN COMPARATOR

Plants of the new cultivar 'OVPEARLS01' differ from the closest known comparator, *Echeveria* 'Purple Pearl' (Community Plant Variety Rights Office grant number 2008/2720), which is also the closest known comparator, in the following characteristics described in Table 2 below.

TABLE 2

| Characteristic | 'OVPEARLS01' | 'Purple Pearl' |
|---|---|---|
| Plant height. | Taller than 'Purple Pearl. | Shorter than 'OVPEARLS01'. |
| Leaf attitude. | More upright. | Less upright. |
| Leaf aspect. | More concave. | Less concave. |
| General coloration of the aging foliage. | Older leaves are more suffused with green. | Older leaves are less suffused with green; retaining the bluish coloration. |

That which is claimed is:

1. A new and distinct variety of *Echeveria* plant named 'OVPEARLS01', substantially as described and illustrated herein.

* * * * *